(12) United States Patent
Hesson et al.

(10) Patent No.: US 6,689,756 B2
(45) Date of Patent: Feb. 10, 2004

(54) TREATMENT OF NEUROLOGICAL DISEASE

(75) Inventors: David P. Hesson, Malvern, PA (US); Timothy J. Pelura, Malvern, PA (US); Glen D. Frazer, Wynnewood, PA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 167 days.

(21) Appl. No.: 10/090,442

(22) Filed: Mar. 4, 2002

(65) Prior Publication Data

US 2003/0022879 A1 Jan. 30, 2003

Related U.S. Application Data

(60) Provisional application No. 60/331,359, filed on Mar. 2, 2001.

(51) Int. Cl.⁷ .......................... A61K 31/70; A61K 31/43
(52) U.S. Cl. ........................................ 514/43; 514/192
(58) Field of Search ................... 514/43, 192

(56) References Cited

U.S. PATENT DOCUMENTS

| | | |
|---|---|---|
| 4,445,500 A | 5/1984 | Osterholm |
| 4,445,886 A | 5/1984 | Osterholm |
| 4,445,887 A | 5/1984 | Osterholm |
| 4,445,888 A | 5/1984 | Osterholm |
| 4,446,154 A | 5/1984 | Osterholm |
| 4,446,155 A | 5/1984 | Osterholm |
| 4,450,841 A | 5/1984 | Osterholm |
| 4,451,251 A | 5/1984 | Osterholm |
| 4,657,532 A | 4/1987 | Osterholm |
| 4,686,085 A | 8/1987 | Osterholm |
| 4,758,431 A * | 7/1988 | Osterholm .................. 424/149 |
| 4,963,130 A | 10/1990 | Osterholm |
| 4,981,691 A | 1/1991 | Osterholm |
| 5,085,630 A | 2/1992 | Osterholm |
| 6,500,809 B1 * | 12/2002 | Frazer ........................ 514/54 |

FOREIGN PATENT DOCUMENTS

WO 01/39819 * 6/2001

OTHER PUBLICATIONS

Haley, Jr. et al., "Treatment of Experimental Brain Abscess with Penicillin and Chloramphenicol", Journal of Infectious Diseases 148(4), pp. 737–744 (1983).*

* cited by examiner

Primary Examiner—Kevin E. Weddington
(74) Attorney, Agent, or Firm—Dechert LLP

(57) ABSTRACT

Provided is, among other things, a method of treating in an animal infection or neoplasm of cerebrospinal tissue characterized by a risk of death, the method comprising: (a) injecting a physiologically acceptable fluid for cerebrospinal perfusion into a first catheter into the cerebrospinal pathway, which fluid for cerebrospinal perfusion has an therapeutically effective amount an agent, the agent selected for effectiveness against the infection as identified or diagnosed; (b) withdrawing fluid at a second catheter into the cerebrospinal pathway to create a flow and flow pathway between the first and second catheters; and (c) maintaining the flow for a period of time adapted to perfuse at least 1 CSF volume.

28 Claims, No Drawings

TREATMENT OF NEUROLOGICAL DISEASE

TREATMENT OF NEUROLOGICAL DISEASE

This application claims the priority of U.S. provisional application Ser. No. 60/331,359 (pursuant to a petition converting U.S. patent application Ser. No. 09/798,774 to a provisional), which application was filed Mar. 2, 2001.

This invention relates to antimicrobial and antineoplastic formulations or compositions useful for treating neurologic infections and cancers.

The cerebrospinal fluid (CSF) pathway system, which intimately bathes and permeates brain and spinal cord tissues, constitutes a circulatory system within the body. Although it has some similarities to systemic vascular and lymphatic circulation, its anatomical arrangement differs considerably. Indeed, this system has been named the "third circulation" system. Due to the extensive area of CSF-tissue contact over the cerebral and spinal cord surfaces, in the paravascular Virchow-Robins spaces, and cerebral ventricles, the cerebrospinal fluid system constitutes a vast, complex and intimate avenue for access to central nervous tissue.

Disclosed herein are methods of treating critical infections and cancers of neuronal tissue using a perfusion of that tissue, methods of scrubbing out toxins and infectious particles, organisms or cells with appropriate fluids, methods of treating certain infections or treating certain cancers, and methods of delivering certain classes of agents. These methods are not disclosed in such documents as U.S. Pat. No. 4,758,431, which assert without discussion that one can incorporate an antibiotic or antineoplastic into an oxygenating emulsion. An intermittent perfusion like administration of the antineoplastic agent ACNU (3-[(4-amino-2-methyl-5-pyrimidinyl)-methyl]-1-(2-chloroethyl)-1-nitrosourea hydrochloride, nimustine) that involves an Omaya reservoir and lumbar puncture was described by Ushio et al (J. Neuro-Oncology 38:207–212, 1998).

SUMMARY OF THE INVENTION

The invention provides, among other things, a method of treating in an animal an infection or cancer of a cerebrospinal tissue characterized by a risk of death, the method comprising: (a) injecting a physiologically acceptable fluid for cerebrospinal perfusion into a first catheter into the cerebrospinal pathway, which fluid for cerebrospinal agent, the agent selected for effectiveness against the disease as identified or diagnosed; (b) withdrawing fluid at a second catheter into the cerebrospinal pathway to create a flow and flow pathway between the first and second catheters; and (c) maintaining the flow for a period of time adapted to perfuse at least 1 CSF volume.

Also provided is a method of treating in an animal an infection or cancer of a cerebrospinal tissue comprising: (a) injecting a fluid for cerebrospinal perfusion into a first catheter into the cerebrospinal pathway, which fluid has an therapeutically effective amount an antimicrobial or antineoplastic agent, the agent selected for effectiveness against the disease as identified or diagnosed, wherein the fluid for cerebrospinal perfusion further comprises one or both of: (1) an emulsion-forming effective amount of a lipid composition comprised of lipids found in biological membranes, or (2) 0.05–2.0 g/dL albumin; (b) withdrawing fluid at a second catheter into the cerebrospinal pathway to create a flow and flow pathway between the first and second catheters; and (c) maintaining the flow for a period of time adapted to perfuse at least 1 CSF volume.

Further provided is a method of treating bacterial meningitis, bacterial encephalitis, brain abscesses, tuberculous meningitis, neurosyphilis, fungal meningitis or meningoencephalitis, parasitic CNS infections or viral CNS infections comprising: (a) injecting a physiologically acceptable fluid for cerebrospinal perfusion into a first catheter into the cerebrospinal pathway, which fluid for cerebrospinal perfusion has an infection-treating effective amount an antimicrobial agent, the antimicrobial agent selected for effectiveness against the infection as identified or diagnosed; (b) withdrawing fluid at a second catheter into the cerebrospinal pathway to create a flow and flow pathway between the first and second catheters; and (c) maintaining the flow for a period of time adapted to perfuse at least 1 CSF volume.

Additionally provided is a method of treating in an animal an infection of cerebrospinal tissue comprising: (a) injecting a fluid for cerebrospinal perfusion into a first catheter into the cerebrospinal pathway, which fluid has an infection-treating effective amount an antimicrobial agent, the antimicrobial agent selected for effectiveness against the infection as identified or diagnosed, wherein the antimicrobial agent is an antihelminthic, aminoglycoside antibacterial, amphenicol antibacterial, ansamycin antibacterial, β-lactam antibacterial, lincosamide antibacterial, macrolide antibacterial, polypeptide antibacterial, tetracycline class antibacterial, cycloserine antibacterial, tuberin, quinolone class antibacterial, sulfonamide antibacterial, tuberculostatic antibacterial, antifungal, antiprotazoal or antiviral agent; (b) withdrawing fluid at a second catheter into the cerebrospinal pathway to create a flow and flow pathway between the first and second catheters; and (c) maintaining the flow for a period of time adapted to perfuse at least 1 CSF volume.

Further provided is a method of treating neurologic cancers such a gliomas, glioblastomas, astrocytomas, leptomeningeal carcinomas, leptomeningeal leukemia or lymphomas and metastatic cancers from outside the CNS by: (a) injecting a physiologically acceptable fluid for cerebrospinal perfusion into a first catheter into the cerebrospinal pathway, which fluid for cerebrospinal perfusion has an cancer-treating effective amount an antineoplastic agent or agents, the antineoplastic agent selected for effectiveness against the cancer as identified or diagnosed; (b) withdrawing fluid at a second catheter into the cerebrospinal pathway to create a flow and flow pathway between the first and second catheters; and (c) maintaining the flow for a period of time adapted to perfuse at least 1 CSF volume.

Additionally provided is a method of treating in an animal a cancer of the cerebrospinal tissue comprising: (a) injecting a fluid for cerebrospinal perfusion into a first catheter into the cerebrospinal pathway, which fluid has an cancer-treating effective amount an antineoplastic agent, the antineoplastic agent selected for effectiveness against the cancer as identified or diagnosed, wherein the antineoplastic agent is methotrexate (N-[4-[[(2-amino-4-hydroxy-6-pteridinyl)methyl]methylamino]benzoyl]glutamic acid), cytarabine (Ara-C; 4-amino-1-β-D-arabinofuranosylcytosine), thiotepa (triethylenethiophosphoramide or 1,1',1''-phosphinothioylidynetrisaziridine), topotecan ((S)-10-[(dimethylamino)methyl]-4-ethyl-4,9-dihydroxy-1H-pyrano[3',4':6,7]indolizino [1,2-b]-quinoline-3,14(4H,12H)-dione), mafosfamide (an oxazaphosphorine from Baxter Oncology, Frankfurt, Del., which generates its active principle, 4-hydroxy-cyclophosphamide, without hepatic intervention), busulfan (1,4-bis(methanesulfonoxy)butane) or ACNU [(3-[(4-amino-2-methyl-5-pyrimidinyl)-methyl]-1-(2-chloroethyl)-1-nitrosourea hydrochloride]; (b) withdrawing fluid at a second catheter into the cerebrospinal pathway to create a flow and flow pathway between the first and second catheters; and (c) maintaining the flow for a period of time adapted to perfuse at least 1 CSF volume.

Still additionally provided is a method of treating a toxemia of cerebrospinal tissue, comprising: (a) injecting a physiologically acceptable fluid for cerebrospinal perfusion into a first catheter into the cerebrospinal pathway; (b) withdrawing fluid at a second catheter into the cerebrospinal pathway to create a flow and flow pathway between the first and second catheters; and (c) maintaining the flow for a period of time adapted to perfuse (i) at least 15 CSF volumes or (ii) sufficient volume to reduce a concentration of toxin causing the toxemia in the perfusate at least 5-fold.

BRIEF DESCRIPTION OF THE DRAWINGS

FIG. 1 illustrates a perfusion pathway.

DETAILED DESCRIPTION OF THE INVENTION

In addition to providing antibacterial agents into cerebrospinal passageways, the inventive method can also be used to remove infectious organisms, cancer cells and their by-products while optionally providing oxygen, glucose, electrolytes and essential amino acids into neural tissue. If used in a rapidly exchanging cerebrospinal fluid perfusion system, such as is described in WO 01/39819 (the perfusion systems described therein are incorporated by reference, see below), the inventive composition and methods can be used both to supply these nutrients and, at the same time, remove metabolic waste.

Fluid for Cerebrospinal Perfusion

In one embodiment, the fluid for cerebrospinal perfusion ("CSPF") is an oxygen-carrying nutrient emulsion according to the following:

| Component | Preferred Range | More Preferred Range | Still More Preferred Range or Amount |
|---|---|---|---|
| Oxygen-Carrying Compound, % v/v | 5–15 | 9–11 | 9.5–10·5 |
| Lipid, mg/mL | 8–14 | 10–13 | 11.5 |
| Albumin, g/dL, | 0.05–2.0 | 1.5–1.9 | 1.67 |
| α-Ketoglutaric Acid, µg/mL | 5–40 | 22–28 | 25 |
| Amino Acids, µg/mL | | | |
| L-Isoleucine + L-Leucine | 5–50 | 11–23 | 17.5 |
| L-Valine | 5–50 | 11–22 | 16.6 |
| L-Alanine | 5–50 | 19–38 | 28.6 |
| L-Serine | 5–50 | 16–33 | 24.6 |
| L-Histidine | 2–20 | 7–14 | 10.3 |
| L-Methionine | 0.1–5 | 1.4–2.8 | 2.1 |
| L-Phenylalanine + L-Lysine | 5–50 | 23–47 | 35.3 |
| L-Threonine + L-Arginine | 5–50 | 32–64 | 48.3 |
| L-Tyrosine | 1–20 | 5–11 | 7.9 |
| $Na^+$, mM | 135–150 | 137–147 | 147 |
| $K^+$, mM | 2.5–4.0 | 2.7–3.9 | 2.9 |
| $Cl^-$, mM | 110–135 | 116–135 | 130 |
| $Ca^{+2}$, mM | 1.0–1.6 | 1.0–1.5 | 1.15 |
| $Mg^{+2}$, mM | 0.8–1.6 | 1.0–1.5 | 1.12 |
| Glucose (dextrose), mg/dL | 10–150 | 30–100 | 94 |

The pH of the emulsion, or vehicle (constituting the above or the like without oxygen-carrying compound), is in the physiological range, such as about 7.3. In one embodiment, the amino acids include tryptophan.

The fluid for cerebrospinal perfusion is preferably formulated such that it is physiologic and can directly contact tissues of the neuraxis for an extended period of time, from hours to days, without causing side effects. For best performance, it is believed that the artificial cerebrospinal fluid should be appropriately buffered and have appropriate amounts of amino acids, electrolytes and other compounds helpful to healthy metabolism. Thus, in preferred methods, these components do not need to be supplied through equilibration with other body fluids. Of course, simpler solutions, such as appropriately balanced salts, are used in neurosurgery and are to some degree acceptable. Where the fluid for cerebrospinal perfusion is formulated with nutrients, it can be termed "artificial cerebrospinal fluid" or "ACSF."

In some embodiments, the fluid for cerebrospinal perfusion is simplified. For example, the poly-fluorinated, oxygen-carrying compound is omitted, for instance according to the following formulation:

| Component | Preferred Range | More Preferred Range | Still More Preferred Range or Amount |
|---|---|---|---|
| Albumin, g/dL, | 0.05–2.0 | 1.5–1.9 | 1.67 |
| α-Ketoglutaric Acid, µg/mL | 5–40 | 22–28 | 25 |
| Amino Acids, µg/mL | | | |
| L-Isoleucine + L-Leucine | 5–50 | 11–23 | 17.5 |
| L-Valine | 5–50 | 11–22 | 16.6 |
| L-Alanine | 5–50 | 19–38 | 28.6 |
| L-Serine | 5–50 | 16–33 | 24.6 |
| L-Histidine | 2–20 | 7–14 | 10.3 |
| L-Methionine | 0.1–5 | 1.4–2.8 | 2.1 |
| L-Phenylalanine + L-Lysine | 5–50 | 23–47 | 35.3 |
| L-Threonine + L-Arginine | 5–50 | 32–64 | 48.3 |
| L-Tyrosine | 1–20 | 5–11 | 7.9 |
| $Na^+$, mM | 135–150 | 137–147 | 147 |
| $K^+$, mM | 2.5–4.0 | 2.7–3.9 | 2.9 |
| $Cl^-$, mM | 110–135 | 116–135 | 130 |
| $Ca^{+2}$, mM | 1.0–1.6 | 1.0–1.5 | 1.15 |
| $Mg^{+2}$, mM | 0.8–1.6 | 1.0–1.5 | 1.12 |
| Glucose (dextrose), mg/dL | 10–150 | 30–100 | 94 |

In some embodiments, the fluid for cerebrospinal perfusion is simplified further, for instance according to the following table:

| Component | Preferred Range | More Preferred Range | Still More Preferred Range or Amount |
|---|---|---|---|
| Albumin, g/dL, | 0.05–2.0 | 1.5–1.9 | 1.67 |
| $Na^+$, mM | 135–150 | 137–147 | 147 |
| $K^+$, mM | 2.5–4.0 | 2.7–3.9 | 2.9 |
| $Cl^-$, mM | 110–135 | 116–135 | 130 |
| $Ca^{+2}$, mM | 1.0–1.6 | 1.0–1.5 | 1.15 |
| $Mg^{+2}$, mM | 0.8–1.6 | 1.0–1.5 | 1.12 |
| Glucose (dextrose), mg/dL | 10–150 | 30–100 | 94 |

Ions are maintained to the degree required to avoid damage to cerebrospinal tissue. Appropriate amounts of oncotic agents are preferred.

Generally, tissues and cells will not fare well if exposed to large volumes of non-physiologic ionic solutions. Accordingly, appropriate electrolyte compositions at the tissue level are important when it is considered that the circulatory method of the present invention could dilute of electrolytes from the region, to the detriment of cell membrane function. Desirably, sodium, potassium, calcium, magnesium, and chloride ions are carefully balanced in the antimicrobial formulations of the present invention to create, to the degree possible, normal extra-cellular compositions.

The formulations of the invention preferably exclude four amino acids, glutathione, cysteine, ornithine and glutamine, from the group of amino acids included in the formulation, and preferably include sodium bicarbonate in an amount sufficient to increase the buffering capacity of the nutrient solution, in order to more closely resemble cerebrospinal fluid of the subject.

Kits for conveniently and safely generating fluorocarbon nutrient emulsion or a corresponding vehicle lacking polyfluorinated, oxygen-carrying compound are described for example in U.S. patent application No. 09/619,414, filed Jul. 19, 2000 (the specific formulations and kits described therein are incorporated by reference as outlined below).

While not wishing to be limited to theory, it is believed that the lipid and albumin components help flush or perfuse from cerebrospinal tissue infectious organisms, infection-created components, cells and debris that accentuates the generation for septicemic shock. For example, it is believed that these components help flush endotoxin, reducing the generation of cytokines and TNFα, which are believed to lead to shock.

Antimicrobials

Antimicrobial compounds that can be used with the invention include, without limitation, antihelminthic agents, antibacterial agents (such as aminoglycosides, amphenicols, ansamycins, β-lactams [carbacephems, carbapenems, cephalosporins, cephamycins, monobactams, oxacephems, penicillins or others], β-lactamase inhibitors (also called antibacterial adjuncts), lincosamides, macrolides, polypeptides, tetracyclines, quinolones and analogs, sulfonamides or tuberculostatic agents), antiprotozoals, antivirals (such as purines/pyrimidinones, nucleoside analog reverse transcriptase inhibitors, non-nucleoside reverse transcriptase inhibitors (NNRTI's), or HIV protease inhibitors), and antifungals (such as polyene antibiotics, imidazoles, triazoles, others). Particular examples include the following:

| Disease | Drug | Concentration (µg/mL) |
| --- | --- | --- |
| bacterial infections | Amikacin | 1–10 |
| | Gentamicin | 1–10 |
| | Tobramycin | 1–10 |
| | Vancomycin | 3–30 |
| | Rifampin | 0.5–5 |
| | Rifamycin | 1–10 |
| | Chloramphenicol | 6–60 |
| | Amoxicillin | 1–100 |
| | Amoxicillin/clavulanate (Augmentin, SmithKline Beecham) | 1–100 |
| | Ampicillin | 3–30 |
| | Ampicillin/sulbactam (Unasyn, Pfizer) | 1–100 |
| | Penicillin G | 6–60 |
| | Oxacillin | 1–10 |
| | Nafcillin | 1–10 |
| | Methicillin | 5–50 |
| | Piperacillin | 6–60 |
| | Piperacillin/tazobactam (Zosyn, Lederle Laboratories) | 1–100 |
| | Dicloxacillin | 5–50 |
| | Cefotaxime | 30–300 |

-continued

| Disease | Drug | Concentration (µg/mL) |
| --- | --- | --- |
| | Cefuroxime | 30–300 |
| | Ceftriaxone | 30–300 |
| | Cefaperazone | 30–300 |
| | Ceftazidime | 30–300 |
| | Ciprofoxcin | 30–300 |
| | Erythromycin | 10–100 |
| | Streptomycin | 1–10 |
| | Isoniazid | 2–200 |
| | Ethambutol | 5–500 |
| | Ethionizmide or Ethionamide | 2–200 |
| | Pyrazinamide | 2–200 |
| | Metronidazole | 10–100 |
| | Co-Trimoxazole | 10–100 |
| Antivirals | Acyclovir | 1–100 |
| | Idoxuridine | 1–100 |
| | Nevirapine | 1–100 |
| | Didanosine | 1–100 |
| | Abacavir | 0.1–10 |
| | Zidovudine | 0.1–10 |
| | Lamivudine | 0.1–10 |
| | Indinavir | 0.1–10 |
| | Efavirenz (Sustiva ™) | 0.1–10 |
| | Ritonavir | 0.05–0.5 |
| Antifungals | Amphotericin B | 100–500 |
| | Clotrimazole | 1–100 |
| | Flucaonazole | 1–100 |
| | Itraconazole | 1–100 |
| | Ketoconazole | 1–100 |
| | Grieseofulvin | 5–500 |
| | Nystatin | 1–100 |
| | Terbinatine | 1–100 |
| | Flucytosine | 0.1–10 |
| Antimicrobials | Chloramphenicol | 10–100 |
| | Tetracycline | 1–100 |
| | Sulfadiazein | 0.5–5 |
| | Pyrimethamine | 1–100 |
| | Praziquantel | 1–100 |
| | Thiabendazole | 1–100 |

Listed above for a number of the antimicrobial agents are preferred concentration ranges for use in the fluid for cerebrospinal perfusion. Any number of antimicrobial agents can be used, such as those identified on pages THER-9 to THER-17 of the twelfth edition of the Merck Index (incorporated by reference). However, it will be recognized that greater care is taken in selecting a compound for administration by perfusion of neural tissue than would be taken for a less direct administration, such an i.v. administration.

In one embodiment, where the antimicrobial is gentamicin, at least one of the following applies:

1. The fluid for cerebrospinal perfusion is adapted to not carry a respiration-supporting amount of oxygen;
2. The fluid for cerebrospinal perfusion contains at least a preferred amount of lipid and/or albumin;
3. The perfusion with fluid for cerebrospinal perfusion is conducted over the course of 24 hours or less as an adjunct to another antimicrobial therapy.

Antineoplastics

Antineoplastic compounds that can be used with the invention include, without limitation, purine and pyrimidine antimetabolites, antifolates, alkylating agents, topoisomerase I or II inhibitors. Particular examples include the following:

| Disease | Drug | Concentration (μg/mL) |
|---|---|---|
| CNS Leukemia | Methotrexate | 0.1–10 |
| | Cytarabine | 0.1–10 |
| Lymphomatous meningitis | Cytarabine | 0.1–10 |
| | DepoCyt (sustained release, liposomal formulation of Cytarabine from Chiron Corp., Emeryville, CA) | 1–100 |
| Neoplastic meningitis | Thiotepa | 1–100 |
| Leukemia's and | Topotecan | 0.01–1 |
| Solid tumors | Mafosfamide | 1–10 |

[DepoCyt: weight of Cytarabine or Cytarabine + lipids?]

Diseases

Non-viral infections of the CNS are considered to be infections caused by bacteria, mycobacteria, fungi, and parasitic organism. Common bacterial meningitis can be caused by organisms such as *Haemophilus influenzae, Neisseria meningitides, Streptococcus pneumoniae, Listeria monocyogenes, Staphylococcus aureus,* group *A streptococci,* and others. Bacterial encephalitis can be caused by organisms such as *Mycoplasma pneumoniae* and *Listeria monocytogenes,* and others. Brain abscesses can be caused by organisms Bacteroides, Propionbacterium, *E. coli,* Proteus, Staphylococci, *Haemophilus influenzae,* Actinomyces and Nocardia, and others. Tuberculous meningitis can be caused by organisms such as *Mycobacterium tuberculosis* and *Mycobacterium bovis.* Neurosyphilis can be caused by the organism *Treponema pallidum.* Fungal infections of the CNS can give cause meningitis, meningoencephalitis and/or brain abscesses. These infections are most commonly caused by *Candida albicans, Cryptococcus neoformans,* Aspergillus, and *Coccidioides immitis,* and others. CNS infections can also be caused by parasites such as rickettsias, protozoa and worms. These parasites manifest them selves with diseases such as Typhus, Rocky Mountain Spotted Fever, Q Fever, Toxoplasmosis, Cerebral Malaria, Trichinosis, Trypanosomiasis, Cysticercosis and Schistosomiasis. The invention is believed to be particularly suitable for treating the diseases listed here.

The invention is also believed useful for viral infections of the CNS tissue, such as HIV or Herpes Zoster infections.

Methodology

In accordance with a preferred method of the present invention, the antimicrobial or antineoplastic formulation is circulated through this cerebrospinal fluid route by injecting it into brain vesicles and withdrawing it from the cisterna magna or the spinal subarachnoid space to nourish and to treat central nervous tissues. In other instances the fluid can be injected into the subarachnoid space and withdrawn from another subarachnoid position. In a preferred embodiment, oxygenated antimicrobial formulation can be circulated to tissues to be treated in amounts sufficient to provide adequate gas exchange. Where one seeks to perfuse sufficiently to remove toxin, cells or debris, an antimicrobial or antineoplastic agent is optional.

The fluid for cerebrospinal perfusion (for example comprising an antimicrobial or antineoplastic agent) can be introduced into the subarachnoid spaces through a catheter that transverses the skull or spinal column and the meninges. The delivery point can be the lateral ventricles, subarachnoid space around the brain, cisterna magna or anywhere along the spine. The fluid for cerebrospinal perfusion can be withdrawn from the subarachnoid space from any of these locations using a similar catheter. The fluid for cerebrospinal perfusion can be returned to the delivery system, reconditioned as necessary to add components that have been consumed or remove undesirable components that have accumulated, and then returned to the subarachnoid space in recirculating fashion. This process can be continued for days if necessary, thereby directly exposing the neuraxis to the agent over an extended period of time.

Where one seeks to flush out toxins, cells or infectious organisms or particles, the fluid for cerebrospinal perfusion is preferably not recirculated. For example, in some embodiments, the withdrawn fluid for a first 4–8 CSF volumes is preferably not recirculated by injection at the first catheter.

This method has several advantages over other routes of administration, such as direct exposure of the nervous system tissue to the antimicrobial or antineoplastic agent by a simple bolus injection of the agent into the subarachnoid space. This invention provides a method of circulating the antimicrobial or antineoplastic agent throughout the neuraxis, thus exposing nervous system tissue to the agent more uniformly than would otherwise be possible. It also provides a method of maintaining the antimicrobial or antineoplastic agent within a narrow concentration range, avoiding the necessity of high bolus concentrations over time. According to this method, the nervous system tissue can be exposed to the agent for extended period time, such as days, if necessary. Further, this method minimizes the amount of drug necessary to achieve a therapeutic effect.

It is preferable to establish a flow pathway from the entry catheter (e.g., a ventricular catheter into a lateral ventricle of the brain) to an exit point at a different location in the cerebral spinal pathway (e.g., into the intrathecal space of the lumbar (such as L4–L5) region of the spine) without prematurely inserting an fluid for cerebrospinal perfusion containing, for example, antimicrobial agent, oxygen-carrying compound, other emulsified components, or the like.

As illustrated in FIG. 1, a ventricular catheter 1 is inserted into a lateral ventrical 2. Via aqueduct 3, cisterna magna 4 and subarachnoid spaces 5, a flow pathway can be established to a lumbar outflow catheter 6. When the inflow and outflow catheters are established (typically with suitable controls to monitor intracranial and intraspinal pressure), vehicle can be used to establish the existence of a flow pathway (such as that illustrated) from the inflow catheter to the outflow catheter. Preferably, the vehicle is infused under gravity feed, with the pressure head designed to avoid excessive intracranial pressure. Once established, the vehicle can be substituted with the fluid for cerebrospinal perfusion.

It will be apparent that more than two catheters can be used, though additional catheters are not particularly preferred. Care is taken to monitor the intracranial pressure to assure that flow rates do not cause excessive pressure.

Fluid for cerebrospinal perfusion is preferably perfused through the cerebrospinal pathway for a period of time or for a flush volume adapted to effectively reduce the concentration of microbes, microbe products, or other molecular or debris components resulting from infection. Included among the components that can be reduced with the methodology of the invention are immune or other signaling molecules that are associated with adverse consequences such as septicemic shock. The volume perfused can be about 15 CSF volumes, where a "CSF volume" is the average volume of CSF fluid found in animals of comparable age to the subject. Preferably, at least about 1, 2, 4, 8, 15 or 30 CSF volumes are used. In adult humans, for example, a flow rate in the range of 300–3,600 mL/hr is expected, resulting in the exchange of about 2–22 CSF volumes/hr. In human adults, the perfusion is preferably with 300 to 3,600 mL/hr.

Where one seeks to perfuse sufficiently to remove a toxin, perfusion can be maintained for an amount of time or volume effective to diminish toxin concentration at least about 5–50-fold, preferably at least about 10-fold. It will be recognized that the initial "perfusate" against which the reduction is measured is the initial CSF, or that portion of the initial CSF having the highest concentration of toxin.

The perfusion can be conducted, for example, for 6, 12, 24 or 48 or more hours. Preferably the perfusion is conducted for between 6 hours and 48 hours or between 12 hours and 24 hours. More preferably, the perfusion is conducted for at least about 24 hours. Preferably, the perfusion is conducted for no more than about 120 hours (or, in some embodiments, no more than about 72 hours).

In one embodiment, the perfusion is an adjunct to a longer term therapy that primarily seeks to deliver the antimicrobial agent, and does not seek to perfusion out the cerebrospinal tissue. For example, at some point during the course of the infection the perfusion is conducted to reduce the quantity of infectious organisms. Thereafter, the focus is typically on delivery of the antimicrobial agent, rather than perfusing fluid and delivering antimicrobial agent. It will be recognized that where the catheters are left in place, these can be used to deliver antimicrobial agent by injecting for example 0.1, 0.2, 0.4, 1 or 2 or 5 CSF volumes or less. In some cases, the longer-term delivery will be by a less invasive method, such as intravenous, oral, or any other recognized method of delivery. The post-perfusion administrations are typically done at least daily for at least seven days. If additional perfusions are conducted in this embodiment, the number of perfusions is typically small, such as two or three in total (including the original perfusion).

Preferred treatment subjects among animals are mammals, preferably humans.

Analysis of Microbial Susceptibility

A sampling of infected CSF can be collected and assayed for susceptibility to antimicrobial agent. The initial fluid for cerebrospinal perfusion injected to cause the efflux of the CSF can be formulated without antimicrobial agent to assure that such antimicrobial does not interfere with the susceptibility measurement. Or, the collection of CSF for testing can be cutoff before any overlap with fluid for cerebrospinal perfusion which may contain antimicrobial. After conducting susceptibility studies, an antimicrobial composition selected based on the studies can be mixed into the fluid for cerebrospinal perfusion, or the fluid for cerebrospinal perfusion being inserted can be replaced with fluid for cerebrospinal perfusion formulated with the identified antimicrobial composition.

In some embodiments, the perfusion is conducted while susceptibility studies are conducted. The perfusion preferably but not necessarily contains an antimicrobial agent selected from diagnostic information initially available. After susceptibility studies have been conducted, the antimicrobial composition identified can be administered by a new perfusion, non-perfusion use of the catheters to inject fluid for cerebrospinal perfusion with the antimicrobial, or another route of administration. In other embodiments, the initial injection of fluid for cerebrospinal perfusion used to obtain CSF is stopped after collection of the CSF, and fluid for cerebrospinal perfusion injection is not resumed until the antimicrobial composition is identified through the susceptibility studies. Susceptibility studies can be conducted, for example, as taught by Clark et al. U.S. Pat. No. 6,096,272.

Oxygen-Carrying Compounds

Generally, the preferred compounds for use as non-aqueous oxygen transfer components are fluorocarbons, such as perfluorocarbons, perfluorinated alkyl polyethers, fluoroethers, fluoramines, bromofluorocarbons, chlorofluorocarbons, and the like. While compounds within these groups range in molecular weight from 250 to 7000, their selection for use as non-aqueous transport components are based upon the combination of features of the proper vapor pressure, molecular weight, viscosity, and emulsifiability, emulsion stability and tissue distribution. Not only do fluorocarbons possess appropriate properties but they are for the most part non-toxic. One chief advantage of the CSF circulation route is that most or all of the antimicrobial formulation can be removed by washing at the time of treatment termination. In this way long term cellular retention of oxygenating liquids, as previously noted for liver and reticuloendothelial cells in vascular circulations, can be avoided.

Poly-fluorinated, oxygen-carrying compounds are known in the art. The basic requirement is effectiveness in carrying physiologically useful amounts of oxygen. Factors involved in selecting preferred such compounds include oxygen capacity, tissue retention (preferably minimized), emulsion stability, toxicity, and the like. Such compounds are described, for example, in: Riess et al., "Design Synthesis and Evaluation of Fluorocarbons and Surfactants for In vivo Applications New Perfluoroalkylated Polyhydroxylated Surfactants", *Biomat. Artif. Cells Artif. Organs,* 16:421–430 (1988); Riess, Reassessment of criteria for the Selection of Perfluorochemicals for Second-Generation Blood Substitutes: Analysis of Structure/Property Relationships, *Artificial Organs* 8:44–56 (1984); Riess, et al., Design, Synthesis and Evaluation of Fluorocarbons and Surfactants for In Vivo Applications New Perfluoroalkylated Polyhydroxylated Surfactants, *Biomat. Artif. Cells Artif Organs* 16:421–430 (1988); Riess, et al., Solubility and Transport Phenomena in Perfluorochemicals Relevant to Blood Substitution and Other Biomedical Applications, *Pure & Applied Chem.,* 54:2383–2406 (1982); Yamanouchi, et al., Quantitative Structure-In Vivo Half-Life Relationships of Perfluorochemicals for Use as Oxygen Transporters, *Chem., Pharm. Bull.,* 33:1221–1231 (1985); Lowe, et al., Perfluorochemicals: Blood Substitutes and Beyond *Adv. Mater,* 3:87–93 (February, 1991); Riess, et al., Fluorocarbon-Based In Vivo Oxygen Transport and Delivery Systems *Vox Sang,* 61:225–239 (December 1991); and Weers, et al., U.S. Pat. No. 5,914,352.

Among preferred poly-fluorinated, oxygen-carrying compounds are those of the formula

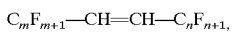

$$C_mF_{m+1}-CH=CH-C_nF_{n+1},$$

where m and n or independently at least 1 and m+n equals 6 to 10. Preferably, the double bond is trans. One preferred poly-fluorinated, oxygen-carrying compound is trans-Bis-perfluorobutyl ethylene (m and n each equal 4), which is also known as F44E. F44E formulations have a 25% greater oxygen carrying capacity than that of a prior nutrient solution made with perfluorodecalin, Bell et al., Neurology 37:133, 1987. Formulations comprising F44E are less viscous and relatively easier to perfuse.

Also preferred are those of the formula

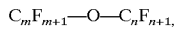

where m and n or independently at least 1 and m+n are equals 6 to 9 (or 8). One of the perfluoro alkyls can be substituted with a halo from Br (preferably), Cl or I. Further preferred are those of the formula

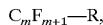

where m is 8 (or 10) to 12 and R is Br, Cl, I, or $C_1$–$C_3$ alkyl.

Besides fluorocarbon based products, cell-free hemoglobin and liposome encapsulated hemoglobin may also be used as artificial oxygen carriers. Hemoglobin is a 4 subunit protein that is the naturally occurring oxygen carrier in red blood cells. Cell-free hemoglobin rapidly dissociates in the bloodstream, so artificial hemoglobins are chemically modified to prevent breakdown. Artificial hemoglobins can be the product of surface modification, crosslinkage, or polymerization. The production and use of cell-free hemoglobin is detailed in U.S. Pat. Nos. 5,438,041; 5,770,727; 5,952,470; 5,691,453; 5,618,919; 5,599,907; 5,739,011; 5,563,254; 5,449,759; 5,128,452; 5,827,693, and 5,312,808. Hemoglobin can also be prevented from degradation by being encapsulated within a protective barrier, as in the case with liposome encapsulated hemoglobin, the production and use of which is presented in U.S. Pat. Nos. 5,049,391; 4,133,874; 4,776,991; 4,425,334, and 4,532,130.

Definitions

The following terms shall have, for the purposes of this application, the respective meanings set forth below.

antimicrobial agent. An antimicrobial agent is a bioactive agent that inhibits the reproduction or decreases the survival of pathogenic microbes (e.g., a bacteria, mycoplasma, fungi including but not limited to yeast, virus, protozoa or parasite (such as a nematode, schistosome, malaria parasite)) or inhibits the propagation, which includes without limitation replication, viral assembly or cellular infection, of a virus.

bioactive agent. A bioactive agent is a substance such as a chemical that can act on a cell, virus, tissue, organ or organism, including but not limited to insecticides or drugs (i.e., pharmaceuticals) to create a change in the functioning of the cell, virus, organ or organism. In preferred embodiments of the invention, methods of identifying bioactive agents of the invention are applied to organic molecules having molecular weight of about 1500 or less.

effective amount: The meaning of "effective amount" will be recognized by clinicians but includes an amount effective to reduce, ameliorate or eliminate one or more symptoms of the disease sought to be treated or the condition sought to be avoided or treated, or to otherwise produce a clinically recognizable change in the pathology of the disease or condition.

endotoxin. An endotoxin is a heat stable polysaccharide-like inflammation-causing agent found in or derived from bacterial cell membranes. The term is often used more specifically to refer to lipopolysaccharide (LPS) of the outer membrane of gram-negative bacteria. There are three parts to the molecule, Lipid A (multiple (such as six) fatty acid residues linked to a core typically including two glucosamine residues), core oligosaccharide (e.g., a branched chain of ten sugars) and a variable length polysaccharide side chain (up to 40 sugar units in smooth forms). The variable length polysaccharide can be removed without affecting the toxicity (rough LPS). Some endotoxin is believed to be released into the medium and endotoxin is responsible for many of the virulent effects of gram-negative bacteria.

exotoxin. Any agent released from a microbe that has toxic effect, including toxicity through inducing an inflammatory response. A number of exotoxins act by injecting an ADP-ribosylating activity into target cells. For example, diphtheria toxin and exotoxin A of *P. aeruginosa* are believed to act by this mechanism.

nutrient-providing effective amount. A nutrient-providing effective amount of a substance is an amount that can be expected, provided sufficient amounts of other nutrients, to increase metabolism or reproduction of mammalian cells compared with nutrient solutions lacking that substance.

oncotic agent. By oncotic agent is meant substances, generally macromolecules, that are of a size that is not readily able to leave the body cavity or other fluid containing body spaces (such as the cerebrospinal pathway, including the cerebral ventricles and subarachnoid spaces) into which they are inserted. Such oncotic agents are exemplified by blood plasma expanders which are known in general as macromolecules having a size sufficient to inhibit their escape from the blood plasma through the circulatory capillary bed into the interstitial spaces of the body. Serum albumin, preferably human serum albumin, is one well known blood plasma protein that can be used as an oncotic agent. Polysaccharide blood plasma expanders are often glucan polymers. For example, Hetastarch (a product of American Home Products) is an artificial colloid derived from a waxy starch composed almost entirely of amylopectin with hydroxyethyl ether groups introduced into the alpha (1–4) linked glucose units. The colloid properties of a 6% solution (wt/wt) of hetastarch approximate those of human serum albumin. Other polysaccharide derivatives may be suitable as oncotic agents in the blood substitute according to the invention. Among such other polysaccharide derivatives are hydroxymethyl alpha (1–4) or (1–6) polymers and cyclodextrins. In general, it is preferred that the polysaccharide is one that is non-antigenic. High molecular weight agents such as Dextran 70 having a molecular weight of about 70,000 Daltons are generally less preferred because they increase viscosity of the colloidal solution and impair the achievement of high flow rates. Preferably, the oncotic agent is in an amount effective to provide, in conjunction with other components of a fluorocarbon nutrient emulsion or a nutrient solution, an oncotic pressure of one to seven torr.

respiration. Respiration is the physical and chemical processes by which an organism supplies its cells and tissues with the oxygen needed for metabolism and, preferably, relieves them of the carbon dioxide formed in energy-producing reactions.

respiration-supporting amount. A respiration-supporting amount of oxygen is an amount that would, in model experiments, provide a statistically significant reduction in morbidity following a focal ischemic event.

EXAMPLE 1

For treatment of adult pneumococcal or meningococcal meningitis the following formulation is perfused over a 48 hour period.

| Component | Quantity/ 2400 mL |
|---|---|
| Penicillin G | 100 mg |
| F44E | 400 g |
| NaCl, USP | 15.3 g |
| $NaHCO_3$, USP | 4.14 g |
| KCl, USP | 0.46 g |
| $MgCl_2\text{-}6H_2O$, USP | 0.48 g |
| $CaCl_2\text{-}2H_2O$, USP | 0.36 g |
| Egg Yolk Phospholipid | 27.9 g |
| Dextrose, USP | 2 g |
| Albumin (Human), USP (20%) | 40 g |
| L-lysine HCl, USP | 6.48 mg |
| L-alanine, USP | 6.86 mg |
| L-serine, USP | 5.90 mg |
| L-threonine, USP | 7.10 mg |
| L-arginine, USP | 4.48 mg |
| L-leucine, USP | 2.96 mg |
| L-isoleucine, USP | 1.24 mg |
| L-valine, USP | 3.98 mg |
| L-phenylalanine, USP | 1.98 mg |
| L-tyrosine, USP | 1.90 mg |
| L-histidine, USP | 2.46 mg |
| L-methionine, USP | 0.50 mg |
| $NaH_2PO_4$, USP | 8.20 mg |
| $Na_2HPO_4$, USP | 1.22 mg |
| α-ketoglutaric acid | 60 mg |
| Water for Injection, USP | 2081 mL |

EXAMPLE 2

For treatment of adult pneumococcal or meningococcal meningitis the following formulation is perfused over a 48 hour period.

| Component | Quantity/ 2400 mL |
|---|---|
| Chloramphenicol | 200 mg |
| F44E | 400 g |
| NaCl, USP | 15.3 g |
| $NaHCO_3$, USP | 4.14 g |
| KCl, USP | 0.46 g |
| $MgCl_2\text{-}6H_2O$, USP | 0.48 g |
| $CaCl_2\text{-}2H_2O$, USP | 0.36 g |
| Egg Yolk Phospholipid | 27.9 g |
| Dextrose, USP | 2 g |
| Albumin (Human), USP (20%) | 40 g |
| L-lysine HCl, USP | 6.48 mg |
| L-alanine, USP | 6.86 mg |
| L-serine, USP | 5.90 mg |
| L-threonine, USP | 7.10 mg |
| L-arginine, USP | 4.48 mg |
| L-leucine, USP | 2.96 mg |
| L-isoleucine, USP | 1.24 mg |
| L-valine, USP | 3.98 mg |
| L-phenylalanine, USP | 1.98 mg |
| L-tyrosine, USP | 1.90 mg |
| L-histidine, USP | 2.46 mg |
| L-methionine, USP | 0.50 mg |
| $NaH_2PO_4$, USP | 8.20 mg |
| $Na_2HPO_4$, USP | 1.22 mg |
| α-ketoglutaric acid | 60 mg |
| Water for Injection, USP | 2081 mL |

EXAMPLE 3

For treatment of adult pneumococcal or meningococcal meningitis the following non-oxygen carrying formulation is perfused over a 48 hour period.

| Component | Quantity/ 2138 mL |
|---|---|
| Penicillin G | 100 mg |
| NaCl, USP | 15.3 g |
| $NaHCO_3$, USP | 4.14 g |
| KCl, USP | 0.46 g |
| $MgCl_2\text{-}6H_2O$, USP | 0.48 g |
| $CaCl_2\text{-}2H_2O$, USP | 0.36 g |
| Dextrose, USP | 2 g |
| Albumin (Human), USP (20%) | 40 g |
| L-lysine HCl, USP | 6.48 mg |
| L-alanine, USP | 6.86 mg |
| L-serine, USP | 5.90 mg |
| L-threonine, USP | 7.10 mg |
| L-arginine, USP | 4.48 mg |
| L-leucine, USP | 2.96 mg |
| L-isoleucine, USP | 1.24 mg |
| L-valine, USP | 3.98 mg |
| L-phenylalanine, USP | 1.98 mg |
| L-tyrosine, USP | 1.90 mg |
| L-histidine, USP | 2.46 mg |
| L-methionine, USP | 0.50 mg |
| $NaH_2PO_4$, USP | 8.20 mg |
| $Na_2HPO_4$, USP | 1.22 mg |
| α-ketoglutaric acid | 60 mg |
| Water for Injection, USP | 2056 mL |

EXAMPLE 4

For treatment of adult pneumococcal or meningococcal meningitis the following artificial cerebral spinal formulation (ACSF) is perfused over a 48 hour period.

| Component | Quantity/ 2138 mL |
|---|---|
| Penicillin G | 100 mg |
| NaCl, USP | 15.3 g |
| $NaHCO_3$, USP | 4.14 g |
| KCl, USP | 0.46 g |
| $MgCl_2\text{-}6H_2O$, USP | 0.48 g |
| $CaCl_2\text{-}2H_2O$, USP | 0.36 g |
| Dextrose, USP | 2 g |
| L-lysine HCl, USP | 6.48 mg |
| L-alanine, USP | 6.86 mg |
| L-serine, USP | 5.90 mg |
| L-threonine, USP | 7.10 mg |
| L-arginine, USP | 4.48 mg |
| L-leucine, USP | 2.96 mg |
| L-isoleucine, USP | 1.24 mg |
| L-valine, USP | 3.98 mg |
| L-phenylalanine, USP | 1.98 mg |
| L-tyrosine, USP | 1.90 mg |
| L-histidine, USP | 2.46 mg |
| L-methionine, USP | 0.50 mg |
| $NaH_2PO_4$, USP | 8.20 mg |
| $Na_2HPO_4$, USP | 1.22 mg |
| α-ketoglutaric acid | 60 mg |
| Water for Injection, USP | 2056 mL |

EXAMPLE 5

For treatment of adult HIV Brain infection the following non-oxygen carrying formulation is perfused over a 48 hour period.

| Component | Quantity/ 2138 mL |
|---|---|
| Sustiva ™ | 24 mg |
| NaCl, USP | 15.3 g |
| NaHCO$_3$, USP | 4.14 g |
| KCl, USP | 0.46 g |
| MgCl$_2$-6H$_2$O, USP | 0.48 g |
| CaCl$_2$-2H$_2$O, USP | 0.36 g |
| Dextrose, USP | 2 g |
| Albumin (Human), USP (20%) | 40 g |
| L-lysine HCl, USP | 6.48 mg |
| L-alanine, USP | 6.86 mg |
| L-serine, USP | 5.90 mg |
| L-threonine, USP | 7.10 mg |
| L-arginine, USP | 4.48 mg |
| L-leucine, USP | 2.96 mg |
| L-isoleucine, USP | 1.24 mg |
| L-valine, USP | 3.98 mg |
| L-phenylalanine, USP | 1.98 mg |
| L-tyrosine, USP | 1.90 mg |
| L-histidine, USP | 2.46 mg |
| L-methionine, USP | 0.50 mg |
| NaH$_2$PO$_4$, USP | 8.20 mg |
| Na$_2$HPO$_4$, USP | 1.22 mg |
| α-ketoglutaric acid | 60 mg |
| Water for Injection, USP | 2056 mL |

EXAMPLE 6

For treatment of adult HIV Brain infection the following non-oxygen carrying formulation is perfused over a 48 hour period.

| Component | Quantity/2138 mL |
|---|---|
| Acyclovir | 240 mg |
| NaCl, USP | 15.3 g |
| NaHCO$_3$, USP | 4.14 g |
| KCl, USP | 0.46 g |
| MgCl$_2$-6H$_2$O, USP | 0.48 g |
| CaCl$_2$-2H$_2$O, USP | 0.36 g |
| Dextrose, USP | 2 g |
| Albumin (Human), USP (20%) | 40 g |
| L-lysine HCl, USP | 6.48 mg |
| L-alanine, USP | 6.86 mg |
| L-serine, USP | 5.90 mg |
| L-threonine, USP | 7.10 mg |
| L-arginine, USP | 4.48 mg |
| L-leucine, USP | 2.96 mg |
| L-isoleucine, USP | 1.24 mg |
| L-valine, USP | 3.98 mg |
| L-phenylalanine, USP | 1.98 mg |
| L-tyrosine, USP | 1.90 mg |
| L-histidine, USP | 2.46 mg |
| L-methionine, USP | 0.50 mg |
| NaH$_2$PO$_4$, USP | 8.20 mg |
| Na$_2$HPO$_4$, USP | 1.22 mg |
| α-ketoglutaric acid | 60 mg |
| Water for Injection, USP | 2056 mL |

EXAMPLE 7

For treatment of CNS leukemia the following non-oxygen carrying formulation is perfused over a 48 hour period.

| Component | Quantity/2138 mL |
|---|---|
| Methotrexate | 50 mg |
| NaCl, USP | 15.3 g |
| NaHCO$_3$, USP | 4.14 g |
| KCl, USP | 0.46 g |
| MgCl$_2$-6H$_2$O, USP | 0.48 g |
| NaCl$_2$-2H$_2$O, USP | 0.36 g |
| Dextrose, USP | 2 g |
| Albumin (Human), USP (20%) | 40 g |
| L-lysine HCl, USP | 6.48 mg |
| L-alanine, USP | 6.86 mg |
| L-serine, USP | 5.90 mg |
| L-threonine, USP | 7.10 mg |
| L-arginine, USP | 4.48 mg |
| L-leucine, USP | 2.96 mg |
| L-isoleucine, USP | 1.24 mg |
| L-valine, USP | 3.98 mg |
| L-phenylalanine, USP | 1.98 mg |
| L-tyrosine, USP | 1.90 mg |
| L-histidine, USP | 2.46 mg |
| L-methionine, USP | 0.50 mg |
| NaH$_2$PO$_4$, USP | 8.20 mg |
| Na$_2$HPO$_4$, USP | 1.22 mg |
| α-ketoglutaric acid | 60 mg |
| Water for Injection, USP | 2056 mL |

Where noted above, publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of treating in an animal infection of cerebrospinal tissue characterized by a risk of death, the method comprising:
    a. injecting a physiologically acceptable fluid for cerebrospinal perfusion into a first catheter into the cerebrospinal pathway, which fluid for cerebrospinal perfusion has an infection treating effective amount an antimicrobial agent, the antimicrobial agent selected for effectiveness against the infection as identified or diagnosed;
    b. withdrawing fluid at a second catheter into the cerebrospinal pathway to create a flow and flow pathway between the first and second catheters; and
    c. maintaining the flow for a period of time adapted to perfuse at least 1 CSF volume.

2. The method of claim 1, wherein the method is conducted in adult humans and the perfusion volume is 300 to 3,600 mL/hr.

3. The method of claim 1, wherein the flow is maintained for between 6 hours and 48 hours.

4. The method of claim 1, wherein the withdrawn fluid for a first 4 CSF volumes is not recirculated by injection at the first catheter.

5. The method of claim 1, further comprising:
   d. administering to the animal at least daily over the course of at least a week an antimicrobially effective amount of an antimicrobial agent, with the majority of administrations conducted by a route of administration that does not use the catheters or which creates a flow that perfuses no more than 0.1 volume of fluid resident in the cerebrospinal pathway.

6. The method of claim 1, wherein the antimicrobial agent is a penicillin, chloramphenicol, nucleoside analog or non-nucleoside reverse transcriptase inhibitor.

7. A method of treating in an animal an infection of cerebrospinal tissue comprising:
   a. injecting a fluid for cerebrospinal perfusion into a first catheter into the cerebrospinal pathway, which fluid has an infection treating effective amount an antimicrobial agent, the antimicrobial agent selected for effectiveness against the infection as identified or diagnosed, wherein the fluid for cerebrospinal perfusion further comprises one or both of:
      1. an emulsion forming effective amount of a lipid composition comprised of lipids found in biological membranes, or
      2. 0.05–2.0 g/dL albumin;
   b. withdrawing fluid at a second catheter into the cerebrospinal pathway to create a flow and flow pathway between the first and second catheters; and
   c. maintaining the flow for a period of time adapted to perfuse at least 1 CSF volume.

8. The method of claim 7, wherein the flow is maintained for between 6 hours and 48 hours.

9. The method of claim 7, further comprising:
   d. administering to the animal at least daily over the course of at least a week an antimicrobially effective amount of an antimicrobial agent, with the majority of administrations conducted by a route of administration that does not use the catheters or which creates a flow which perfusions no more than 5 volumes of fluid resident in the cerebrospinal pathway.

10. The method of claim 7, wherein the lipids are phospholipids.

11. The method of claim 7, wherein fluid is adapted to not carry a respiration supporting amount of oxygen.

12. A method of treating bacterial meningitis, bacterial encephalitis, brain abscesses, tuberculous meningitis, neurosyphilis, fungal meningitis or meningoencephalitis, parasitic CNS infections or viral CNS infections comprising:
   a. injecting a physiologically acceptable fluid for cerebrospinal perfusion into a first catheter into the cerebrospinal pathway, which fluid for cerebrospinal perfusion has an infection treating effective amount an antimicrobial agent, the antimicrobial agent selected for effectiveness against the infection as identified or diagnosed;
   b. withdrawing fluid at a second catheter into the cerebrospinal pathway to create a flow and flow pathway between the first and second catheters; and
   c. maintaining the flow for a period of time adapted to perfuse at least 1 CSF volume.

13. The method of claim 12, wherein the disease is bacterial meningitis caused by Haemophilus influenzae, Neisseria meningitides, Streptococcus pneumoniae, Listeria monocyogenes, Staphylococcus aureus or group A streptococci.

14. The method of claim 12, wherein the disease is pneumococcal or meningococcal meningitis.

15. The method of claim 14, wherein the antimicrobial agent is penicillin G or chloramphenicol and further fluid components comprise:

| Component | Range |
|---|---|
| α-Ketoglutaric Acid, μg/mL | 5–40 |
| Amino Acids, μg/mL | 5–50 |
| L-Isoleucine + L-Leucine | 5–50 |
| L-Valine | 5–50 |
| L-Alanine | 5–50 |
| L-Serine | 5–50 |
| L-Histidine | 2–20 |
| L-Methionine | 0.1–5 |
| L-Phenylalanine + L-Lysine | 5–50 |
| L-Threonine + L-Arginine | 5–50 |
| L-Tyrosine | 1–20 |
| Na+, mM | 135–150 |
| K+, mM | 2.5–4.0 |
| Cl−, mM | 110–135 |
| Ca+2, mM | 1.0–1.6 |
| Mg+2, mM | 0.8–1.6 |
| Glucose (dextrose), mg/dL | 10–150. |

16. The method of claim 15, wherein penicillin G is present in the fluid at 6–60 μg/mL.

17. The method of claim 15, wherein chloramphenicol is present in the fluid at 6–60 μg/mL.

18. The method of claim 15, wherein the fluid further comprises:

| Component | Range |
|---|---|
| Oxygen Carrying Compound, % v/v | 5–15 |
| Lipid, mg/mL | 8–14 |
| Albumin, g/dL, | 0.05–2.0 . |

19. The method of claim 15, wherein the fluid further comprises:

| Component | Range |
|---|---|
| Albumin, g/dL, | 0.05–2.0. |

20. The method of claim 12, wherein the disease is bacterial encephalitis caused by *Mycoplasma pneumoniae* or *Listeria monocytogenes*.

21. The method of claim 12, wherein the disease is brain abscesses caused by *Bacteroides, Propionbacterium, E. coli, Proteus, Staphylococci, Haemophilus influenzae, Actinomyces, Nocardia, Candida albicans, Cryptococcus neoformans, Aspergillus,* or *Coccidioides immitis*.

22. The method of claim 12, wherein the disease is tuberculous meningitis caused by *Mycobacterium tuberculosis* or *Mycobacterium bovis*.

23. The method of claim 12, wherein the disease is neurosyphilis.

24. The method of claim 12, wherein the disease is fungal meningitis or meningoencephalitis caused by *Candida albicans, Cryptococcus neoformans, Aspergillus,* or *Coccidioides immitis*.

25. The method of claim 12, wherein the disease is Typhus, Rocky Mountain Spotted Fever, Q Fever, Toxoplasmosis, Cerebral Malaria, Trichinosis, Trypanosomiasis, Cysticercosis or Schistosomiasis.

26. The method of claim 12, wherein the disease is an HIV infection or Herpes Zoster infection.

27. A method of treating in an animal an infection of cerebrospinal tissue comprising:
   a. injecting a fluid for cerebrospinal perfusion into a first catheter into the cerebrospinal pathway, which fluid has an infection treating effective amount an antimicrobial agent, the antimicrobial agent selected for effectiveness against the infection as identified or diagnosed, wherein the antimicrobial agent is an antihelminthic, aminoglycoside antibacterial, amphenicol antibacterial, ansamycin antibacterial, β-lactam antibacterial, lincosamide antibacterial, macrolide antibacterial, polypeptide antibacterial, tetracycline class antibacterial, cycloserine, quinolone class antibacterial, sulfonamide antibacterial, tuberculostatic antibacterial, antifungal, antiprotazoal or antiviral agent;
   b. withdrawing fluid at a second catheter into the cerebrospinal pathway to create a flow and flow pathway between the first and second catheters; and
   c. maintaining the flow for a period of time adapted to perfuse at least 1 CSF volume.

28. The method of claim 27, wherein the antimicrobial agent is gentamicin, tobramycin, vancomycin, rifampin, rifamycin, chloramphenicol, amoxicillin, amoxicillin/clavulanate, ampicillin, ampicillin/sulbactam, penicillin g, oxacillin, nafcillin, methicillin, piperacillin, piperacillin/tazobactam, dicloxacillin, cefuroxime, cefiriaxone, cefaperazone, ceftazidime, erythromycin, isoniazid, ethambutol, ethionizmide, pyrazinamide, metronidazole, acyclovir, idoxuridine, amphotericin B, chloramphenicol, tetracycline, sulfadiazein, pyrimethamine, proziquantel, thabedazole, acyclovir or Efavirenz.

* * * * *